United States Patent [19]

Omori

[11] Patent Number: 5,568,503
[45] Date of Patent: Oct. 22, 1996

[54] SOLID-STATE LASER DEVICE WITH OPTICAL FIBER CABLE CONNECTION

[75] Inventor: Shigeru Omori, Nakai-machi, Japan

[73] Assignee: Terumo Kabushiki Kaisha, Tokyo, Japan

[21] Appl. No.: 588,838

[22] Filed: Jan. 19, 1996

Related U.S. Application Data

[63] Continuation of Ser. No. 318,388, Oct. 5, 1994, abandoned.

[30] Foreign Application Priority Data

Oct. 8, 1993 [JP] Japan .................................. 5-253017

[51] Int. Cl.$^6$ ..................................................... H01S 3/08
[52] U.S. Cl. ............... 372/70; 372/75; 372/108; 372/34; 372/71; 606/16; 606/17; 607/89
[58] Field of Search .................... 372/70, 75, 107, 372/108, 34, 6, 71, 35; 606/16, 17; 607/89; 385/117

[56] References Cited

U.S. PATENT DOCUMENTS

| | | |
|---|---|---|
| 4,665,529 | 5/1987 | Baer et al. . |
| 4,979,180 | 12/1990 | Muncheryan . |
| 5,014,279 | 5/1991 | Esterowtiz et al. . |
| 5,437,659 | 8/1995 | Leckrone .................................. 606/7 |

FOREIGN PATENT DOCUMENTS

WO90/16099  12/1990  WIPO .

OTHER PUBLICATIONS

Japanese Patent Application Laid-Open No. 1-167812, published Jul. 3, 1989, with English abstract.
J. A. Morris et al., "Passive Q switching of a diode–pumped Nd:YAG laser with a saturable absorber," *Optics Letters*, vol. 15, No. 8, Apr. 15, 1990, pp. 440–442.
Y. Kimura et al., "Laser–diode–pumped mirror–free $Er^{3+}$ —doped fiber laser," *Optics Letters*, vol. 14, No. 18, Sep. 15, 1989, pp. 999–1001.
J. W. Kuper et al., "Conductively cooled alexandrite laser system," Conference on Laser and Electro-Optics, Jun. 9, 1986, pp. 106–107.

*Primary Examiner*—Rodney B. Bovernick
*Assistant Examiner*—Yisun Song
*Attorney, Agent, or Firm*—Burns, Doane, Swecker & Mathis, LLP

[57] ABSTRACT

This invention has as its object to provide a solid-state laser device which can supply a laser beam pumped by a solid-state laser medium from the distal end of an optical fiber. In order to achieve this object, the solid-state laser device includes a solid-state laser device main body incorporating a semiconductor laser and a first optical system for shaping a first laser beam emitted from the semiconductor laser; an optical fiber cable connected to the solid-state laser device main body and accommodating an optical fiber for guiding the first laser beam shaped by the first optical system; and a solid-state laser medium which is incorporated in the distal end portion, at the light exit side, of the optical fiber cable, and outputs a second laser beam by generating the first laser beam.

13 Claims, 6 Drawing Sheets

SOLID-STATE LASER DEVICE WITH OPTICAL FIBER CABLE CONNECTION

This application is a continuation of Application Ser. No. 08/318,388, filed Oct. 5, 1994, now abandoned.

BACKGROUND OF THE INVENTION

The present invention relates to a solid-state laser device which can be used in the industrial field, medical field, and the like.

A conventional solid-state laser device generally comprises an arrangement wherein an optical fiber is connected to a laser generator to guide a laser beam to an arbitrary position, or an arrangement wherein a laser resonator including a solid-state laser medium is housed in a housing different from that for a pumping light source, and the laser resonator and the light source are connected via an optical fiber so that they can be disassembled from each other, as disclosed in U.S. Pat. No. 4,665,529.

Figure 1:
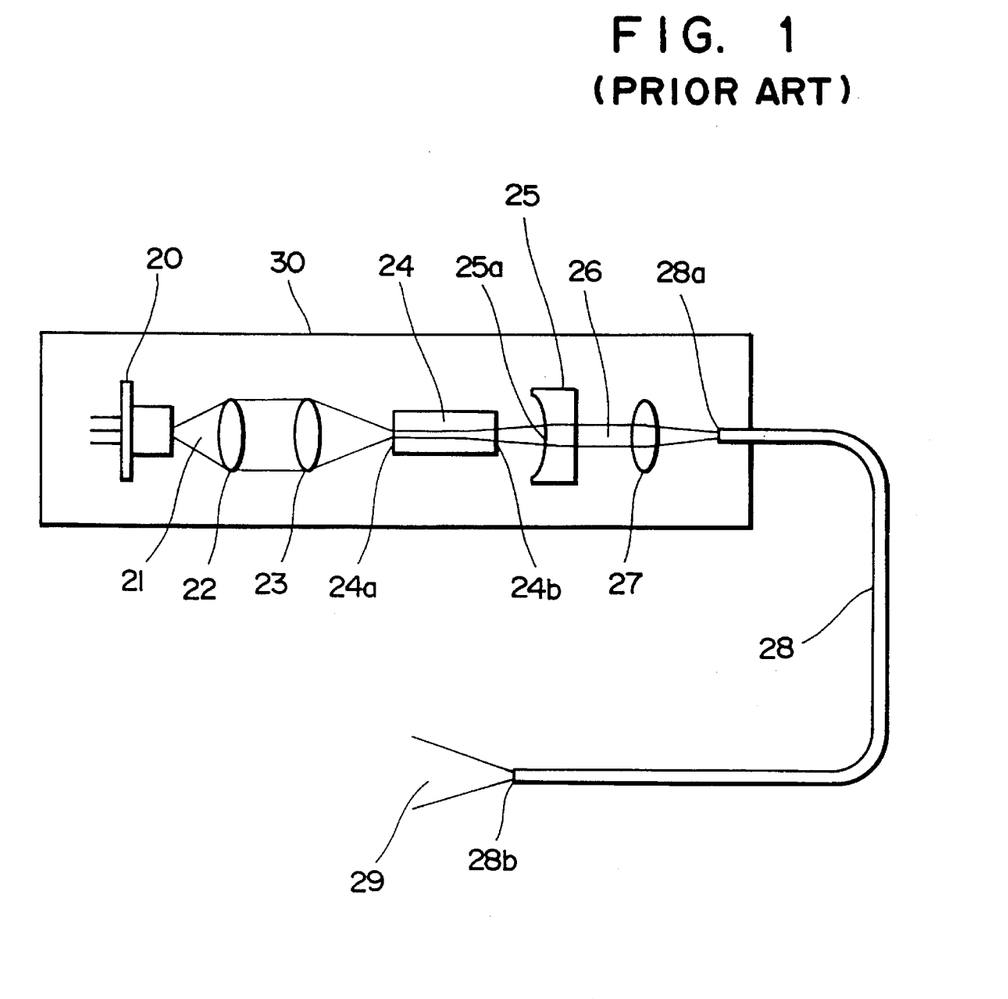
FIG. 1 is a view showing the arrangement of a solid-state laser device of the first prior art.

FIG. 1 shows the arrangement of a conventional solid-state laser device. Reference numeral 20 denotes a semiconductor laser for generating a laser beam having a wavelength of 809 nm; 21, a laser beam emitted from the semiconductor laser 20; 22, a collimator lens; 23, a focusing lens; and 24, a solid-state laser medium (e.g., Nd:YAG). A coating film which has a transmittance of 99.5% for a wavelength of 809 nm and a reflectance of 99.9% for a wavelength of 1.064 µm is formed on a facet 24a of the solid-state laser medium 24, and a coating film which has a transmittance of 99.9% for a wavelength of 1.064 µm is formed on the other facet 24b. Reference numeral 25 denotes a reflection mirror. A coating film which has a reflectance of 97% for a wavelength of 1.064 µm is formed on a facet 25a of the reflection mirror 25. Reference numeral 27 denotes a focusing lens; 28, an optical fiber cable; 29, an output laser beam; and 30, a device main body.

The operation of the conventional solid-state laser device with the above-mentioned arrangement will be explained below. The laser beam 21 having a wavelength of 809 nm, which is generated by the semiconductor laser 20, is shaped into a collimated beam by the collimator lens 22, and the collimated beam is focused on the facet 24b of the solid-state laser medium 24 by the focusing lens 23, thus pumping the solid-state laser medium 24. Light pumped in the solid-state laser medium 24 reciprocates between the facet 24a and the facet 25a of the reflection mirror 25 to cause laser generation, and then emerges from the reflection mirror 25 as a laser beam 26 having a wavelength of 1.064 µm. Thereafter, the laser beam 26 is focused by the focusing lens 27, and is incident on an incident end 28a of the optical fiber cable. The laser beam 26 is guided to a distal end portion 28b via the optical fiber cable 28, and emerges from the optical fiber cable as the output laser beam 29. For this reason, the output laser beam can be irradiated at an arbitrary position separated from the device main body 30.

Figure 2:
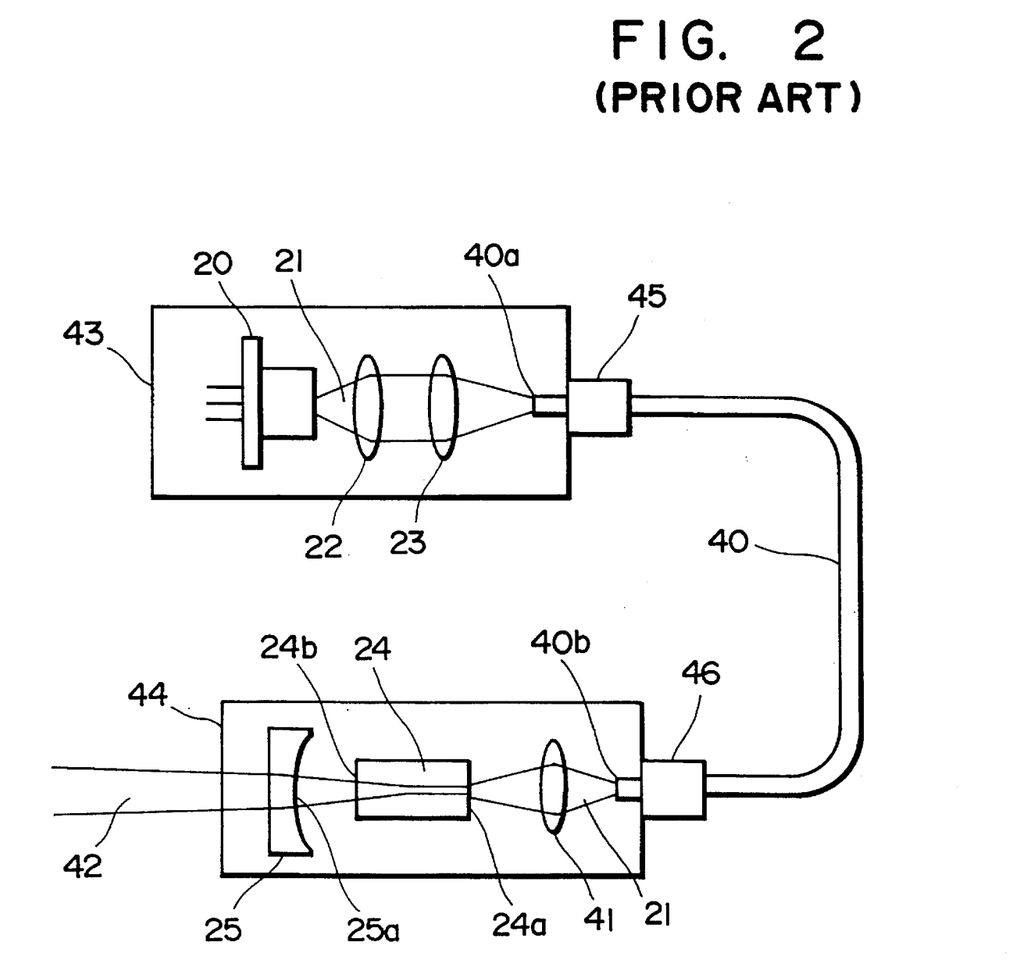
FIG. 2 is a view showing the arrangement of a solid-state laser device of the second prior art.

FIG. 2 shows the arrangement of a second conventional solid-state laser device. Reference numeral 20 denotes a semiconductor laser for generating a laser beam having a wavelength of 809 nm; 21, a laser beam emitted from the semiconductor laser 20; 22, a collimator lens; 23, a focusing lens; and 24, a solid-state laser medium (e.g., Nd:YAG). A coating film which has a transmittance of 99.5% for a wavelength of 809 nm and a reflectance of 99.9% for a wavelength of 1.064 µm is formed on a facet 24a of the solid-state laser medium 24, and a coating film which has a transmittance of 99.9% for a wavelength of 1.064 µm is formed on the other facet 24b. Reference numeral 25 denotes a reflection mirror. A coating film which has a reflectance of 97% for a wavelength of 1.064 µm is formed on a facet 25a of the reflection mirror 25. Reference numeral 40 denotes an optical fiber cable; 41, a focusing lens; 42, an output laser beam having a wavelength of 1.064 µm; 43, a device main body which houses the semiconductor laser 20 and its driving circuit; and 44, a housing which houses a solid-state laser generation unit. Reference numerals 45 and 46 denote optical fiber connectors. The device main body 43, the optical fiber cable 40, and the generation unit housing 44 can be disassembled from each other.

The operation of the second conventional solid-state laser device with the above-mentioned arrangement will be described below. The laser beam 21 having a wavelength of 809 nm, which is generated by the semiconductor laser 20, is shaped into a collimated beam by the collimator lens 22, and the collimated beam is focused by the focusing lens 23. The focused beam is incident on an incident end 40a of the optical fiber cable, and propagates through the optical fiber cable 40. Thereafter, the laser beam 21 emerging from an exit end 40b of the optical fiber cable is focused again by the focusing lens 41 onto the facet 24a of the solid-state laser medium 24, thus pumping the solid-state laser medium 24. Light pumped in the solid-state laser medium 24 reciprocates between the facet 24a and the facet 25a of the reflection mirror 25 to cause laser generation, and then emerges from the generation unit housing 44 via the reflection mirror 25 as the output laser beam 42 having a wavelength of 1.064 µm.

However, according to the examination of the present inventors, in the solid-state laser device having the arrangement of the first prior art, since the light transmission characteristics of the optical fiber have wavelength dependence, when, for example, a quartz optical fiber is used, it is difficult to guide light components in a wavelength range exceeding 2.5 µm and a wavelength range below 300 nm through this fiber, thus preventing a practical application.

In particular, when such a solid-state laser device is used in the medical field, water contents contained in an affected part must be heated to heat the affected part. In order to achieve this object, it is effective to irradiate a laser beam having a wavelength of about 2.8 µm, as a wavelength which is most easily absorbed by water, onto the affected part. More specifically, the above-mentioned device cannot effectively guide a laser beam having a wavelength of 2.8 µm, which is most required in the medical field.

On the other hand, the solid-state laser device having the arrangement in the second prior art aims at replacing the solid-state laser medium or preventing heat generated upon driving of the semiconductor laser in the device main body from influencing the solid-state laser generation unit. For this purpose, the laser generation unit is housed in a housing different from the device main body, and the distal end portion of the fiber has a large size, thus considerably retarding the guiding performance of the generated laser beam to an arbitrary position.

SUMMARY OF THE INVENTION

The present invention has been made in consideration of the above situation, and has as its object to provide a solid-state laser device, which can supply a laser beam pumped by a solid-state laser medium from the distal end of a fiber.

In order to solve the above-mentioned problems and to achieve the above object, a solid-state laser device according to the present invention is characterized by comprising the following arrangement.

That is, a solid-state laser device comprises a solid-state laser device main body incorporating a semiconductor laser and a first optical system for shaping a first laser beam emitted from the semiconductor laser, an optical fiber cable connected to the solid-state laser device main body and accommodating an optical fiber for guiding the first laser beam shaped by the first optical system, and a solid-state laser medium which is incorporated in a distal end portion, at a light exit side, of the optical fiber cable, and generates a second laser beam by pumping by the first laser beam.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENTS (First Embodiment)

Figure 3:
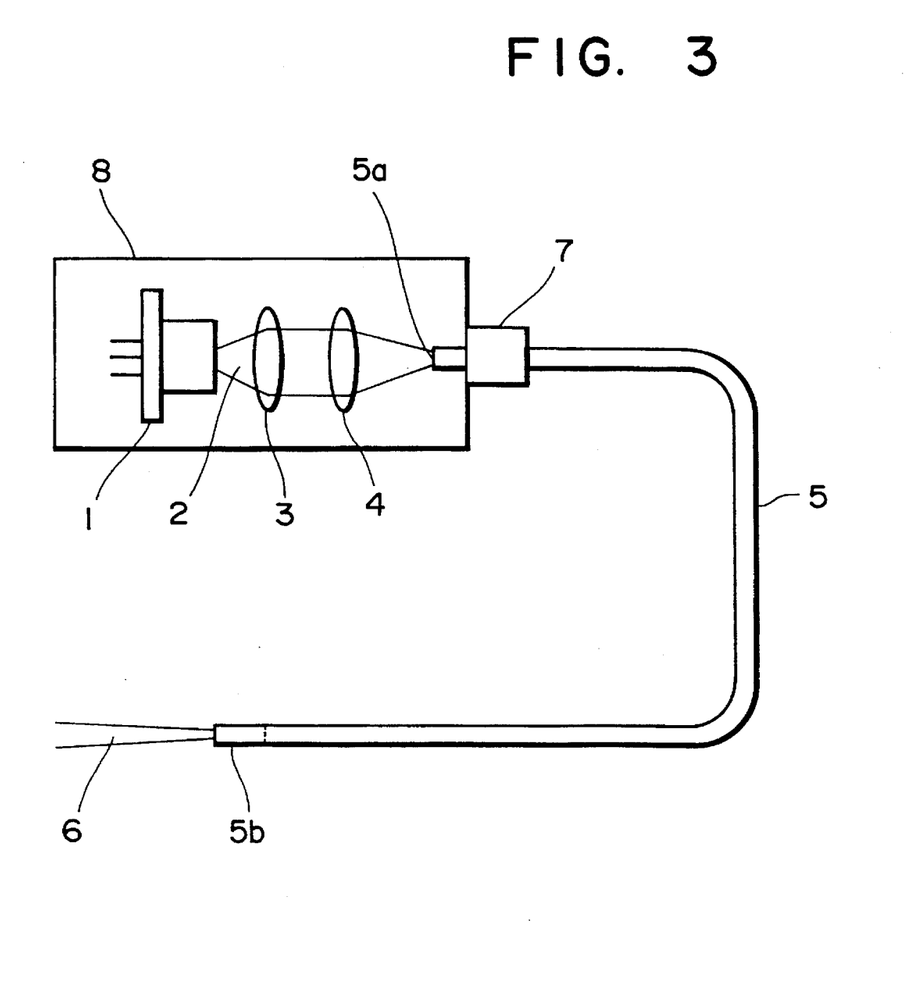
FIG. 3 is a view showing the arrangement of a solid-state laser device according to the first embodiment of the present invention.

FIG. 3 shows the arrangement of a solid-state laser device according to an embodiment of the present invention. Referring to FIG. 3, reference numeral 1 denotes a semiconductor laser for generating a laser beam having a wavelength of 970 nm; 2, a laser beam having a wavelength of 970 nm emitted from the semiconductor laser 1; 3, a collimator lens; 4, a focusing lens; 5, an optical fiber cable; 5a, an incident end of the optical fiber cable; 5b, a distal end portion of the optical fiber cable; 6, an output laser beam having a wavelength of 2.8 μm; and 7, a fiber connector. Reference numeral 8 denotes a housing which houses the semiconductor laser 1 and its driving circuit. The optical fiber cable 5 is connected to the housing 8 of the device main body via the optical fiber connector 7, and can be easily detached therefrom.

Figure 4:
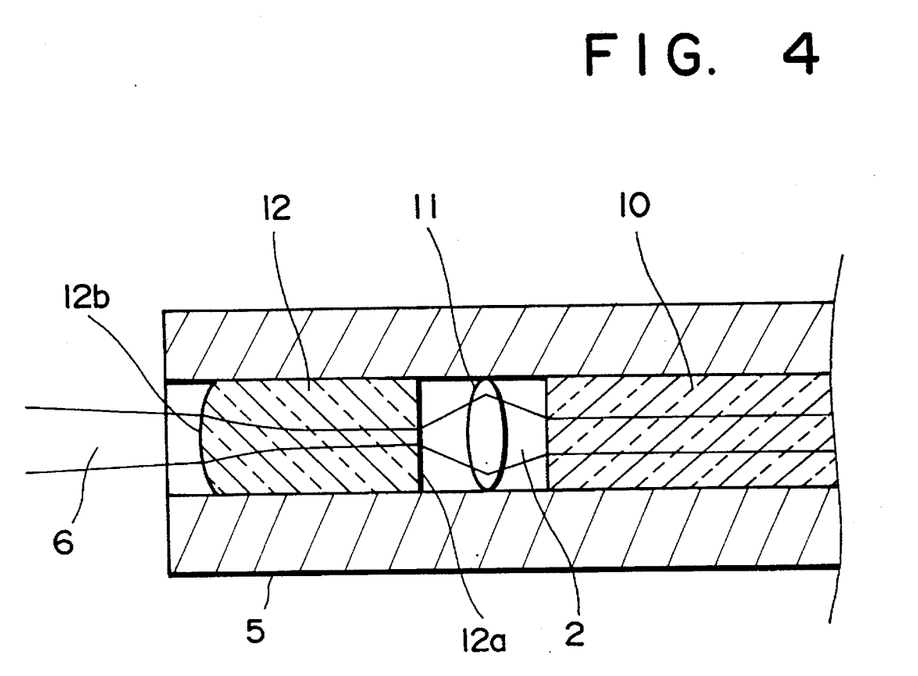
FIG. 4 is a sectional view showing main part of the distal end portion of an optical fiber cable of the solid-state laser device according to the first embodiment of the present invention.

FIG. 4 is a sectional view of the distal end portion 5b of the optical fiber shown in FIG. 3. Reference numeral 10 denotes a quartz optical fiber having a core diameter of 400 μm as an optical fiber; 11, a focusing lens; and 12, a solid-state laser medium (e.g., Er:YLF). A coating film having a transmittance of 99.5% for a wavelength of 970 nm and a reflectance of 99.9% for a wavelength of 2.8 μm is formed on a facet 12a of the solid-state laser medium 12, and a curved surface which has a center on the optical axis and a radius of 20 mm and a coating film having a reflectance of 99.5% for a wavelength of 2.8 μm are formed on the other facet 12b.

The operation of the solid-state laser device with the above-mentioned arrangement will be described below with reference to FIGS. 3 and 4. The laser beam 2 having a wavelength of 970 nm emitted from the semiconductor laser 1 is shaped into a collimated beam by the collimator lens 3, and the collimated beam is focused onto the incident end 5a of the optical fiber cable by the focusing lens 4. The beam then reaches the distal end portion 5b via the optical fiber cable 5. In this case, since the quartz optical fiber 10 in the optical fiber cable 5 has high transmittance for light having a wavelength of 970 nm, the laser beam 2 can be efficiently guided from the incident end 5a to the distal end portion 5b of the optical fiber cable. The laser beam 2 guided to the distal end portion 5b of the optical fiber cable emerges from the quartz optical fiber 10, and becomes incident on the facet 12a of the solid-state laser medium 12 via the focusing lens 11, thus pumping the solid-state laser medium 12. Since the coating films having a high reflectance for light having a wavelength of 2.8 μm are formed on the facets 12a and 12b of the solid-state laser medium 12, as described above, they serve as reflection mirrors of a laser resonator, and light pumped in the solid-state laser medium 12 reciprocates between the facets 12a and 12b to cause laser generation. As a result, the output laser beam 6 having a wavelength of 2.8 μm emerges from the distal end portion 5b of the optical fiber cable.

In this embodiment, the Er:YLF is used as the solid-state laser medium 12. However, the solid-state laser medium 12 may comprise any other media as long as the wavelength of a light source required for pumping the medium can propagate through an optical fiber to be used. For example, Er:YAG, Er:YSGG, or the like may be used. The optical fiber 10 comprises a quartz fiber. However, any other optical fibers may be used as long as they can efficiently guide light from the semiconductor laser 1 to the solid-state laser medium 12. For example, a plastic optical fiber may be used.

(Second Embodiment)

Figure 5:
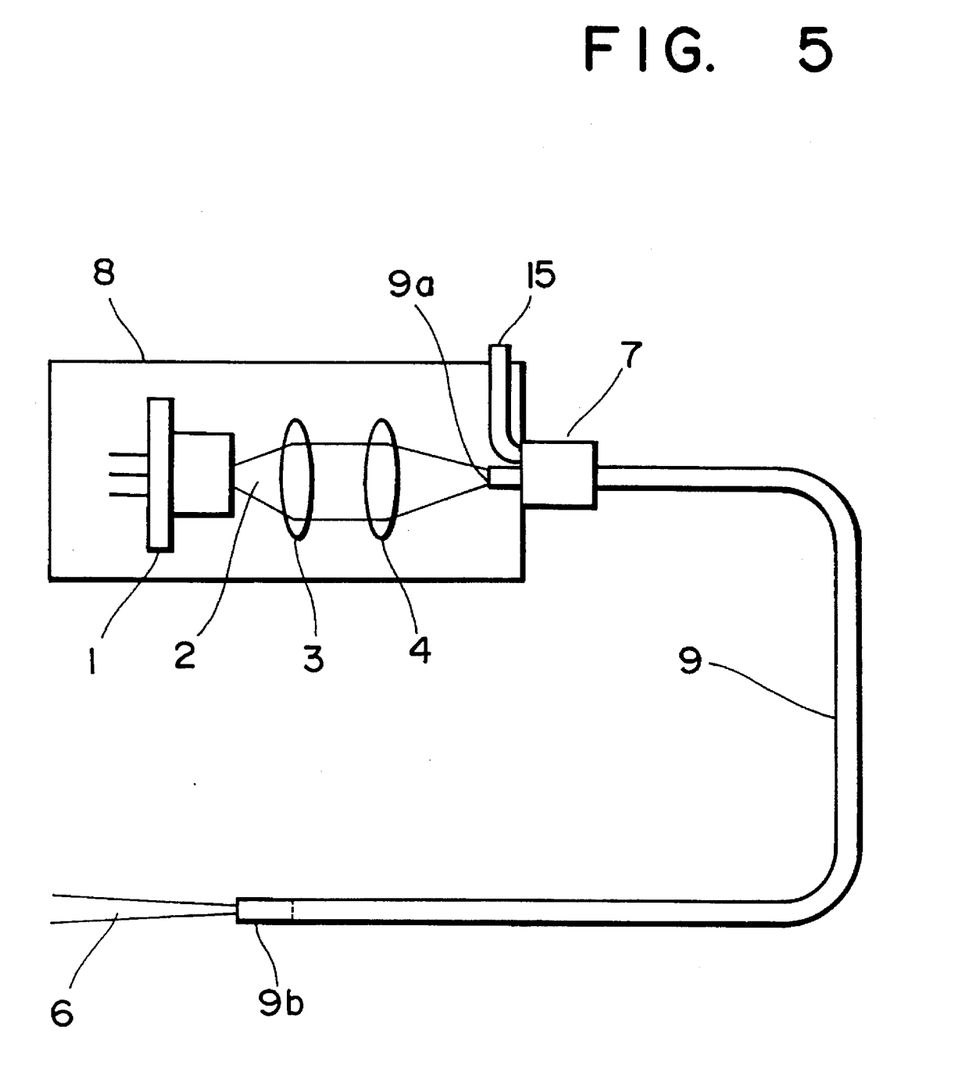
FIG. 5 is a view showing the arrangement of a solid-state laser device according to the second embodiment of the present invention.
Figure 6:
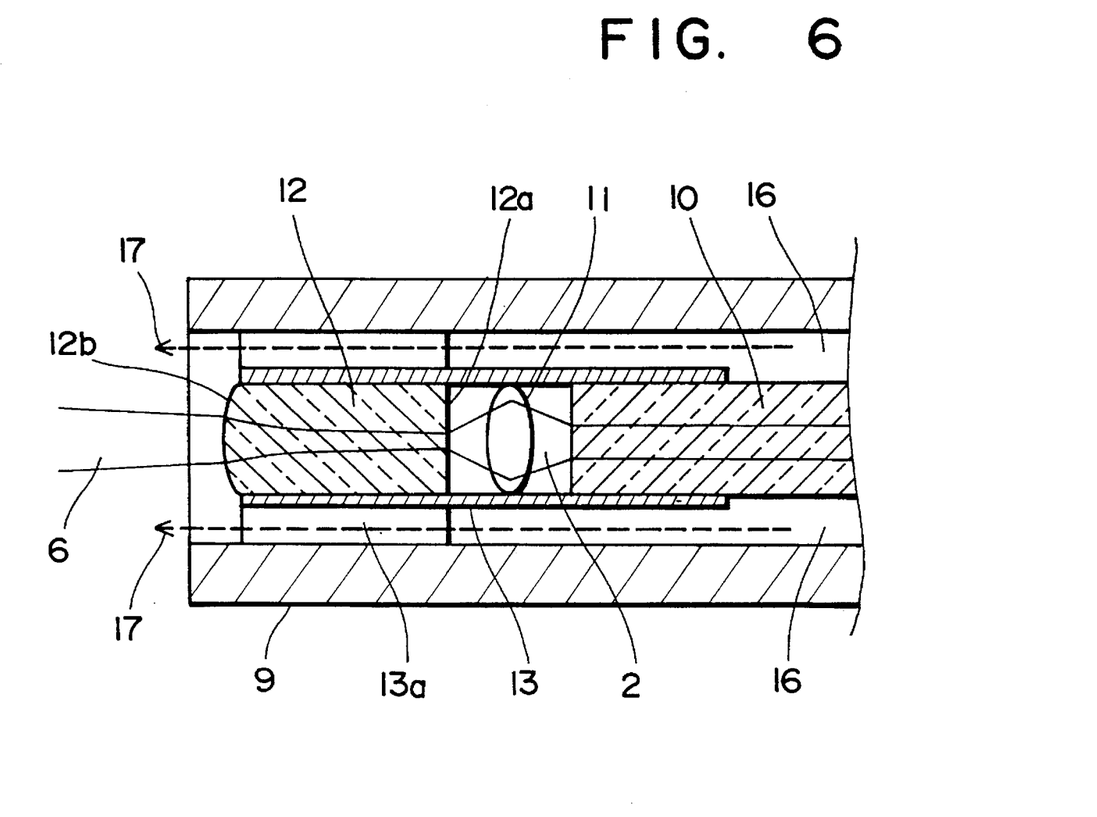
FIG. 6 is a sectional view showing main part of the distal end portion of an optical fiber cable of the solid-state laser device according to the second embodiment of the present invention.

FIG. 5 shows the arrangement of a solid-state laser device according to another preferred embodiment of the present invention, and FIG. 6 shows a section at the distal end portion of an optical fiber cable of the solid-state laser device shown in FIG. 5. Referring to FIG. 5, reference numeral 1 denotes a semiconductor laser for generating a laser beam having a wavelength of 970 nm; 2, a laser beam having a wavelength of 970 nm emitted from the semiconductor laser 1; 3, a collimator lens; 4, a focusing lens; 9, an optical fiber cable; 9a, an incident end of the optical fiber cable; 9b, a distal end portion of the optical fiber cable; 6, an output laser beam having a wavelength of 2.8 μm; 7, a fiber connector; and 15, an injection port for supplying a gas to the optical fiber cable 9. Reference numeral 8 denotes a housing which houses the semiconductor laser 1 and its driving circuit. The optical fiber cable 9 is connected to the housing 8 of the device main body via the optical fiber connector 7, and can be easily detached therefrom. When the optical fiber cable and the housing are connected to each other, the gas injection port 15 and the optical fiber cable 9 are coupled to each other, thus assuring a gas propagation path.

Referring to FIG. 6, reference numeral 10 denotes a quartz optical fiber; 11, a focusing lens; and 12, a solid-state laser medium (e.g., Er:YLF). A coating film having a transmittance of 99.5% for a wavelength of 970 nm and a reflectance of 99.9% for a wavelength of 2.8 μm is formed on a facet 12a of the solid-state laser medium 12, and a curved surface which has a center on the optical axis and a radius of 20 mm, and a coating film having a reflectance of 99.5% for a wavelength of 2.8 μm are formed on the other facet 12b. Reference numeral 2 denotes a pumping laser beam having a wavelength of 970 nm; and 6, an output laser beam having a wavelength of 2.8 μm. Reference numeral 13 denotes a metal holder which surrounds the solid-state laser medium 12, and fixes the focusing lens 11 and the quartz optical fiber 10 on a single optical axis. In this holder 13, fins 13a extending in the circumferential direction are arranged around the solid-state laser medium 12, and the holder 13 is positioned along the inner wall of the distal end portion of the optical fiber cable 9. Reference numeral 16 denotes a gap formed between the optical fiber cable 9 and the holder 13; and 17, an inert gas passing through the gap 16.

The operation of the solid-state laser device with the above-mentioned arrangement will be described below with reference to FIGS. 5 and 6. The generation principle of the solid-state laser device of this embodiment is the same as that in the first embodiment shown in FIGS. 3 and 4. The pumping laser beam 2 having a wavelength of 970 nm is incident on the solid-state laser medium 12 to output the laser beam 6 having a wavelength of 2.8 μm. In this case, the pumping laser beam 2 is absorbed by the solid-state laser medium 12. However, since energy which does not contribute to the above-mentioned laser generation is mainly converted into heat, the temperature of the solid-state laser medium 12 rises, and it becomes difficult to maintain stable laser generation. For this reason, in this embodiment, the gas injection port 15 is formed in a portion, where the optical fiber connector 7 is connected, of the housing 8 of the device main body, and the gap 16 is formed around the solid-state laser medium 12. The inert gas is passed through the gap 16 to cool the solid-state laser medium 12. The holder 13 fixes the solid-state laser medium 12, the focusing lens 11, and the quartz optical fiber 10, and has the heat radiation fins 13a for efficiently radiating the heat of the solid-state laser medium 12.

Note that the above-mentioned inert gas which passes through the gap 16 can also be used as an assist gas for maintaining a good field of view upon irradiation of the laser beam 6 onto an object to be irradiated. The inert gas may be air, and in this case, for example, a compressor as means for generating compressed air can be arranged in or outside the housing 8 of the device main body.

With this arrangement, the semiconductor laser beam 2 as pumping light of the solid-state laser medium is guided to an arbitrary position via the optical fiber cable 5, 9, and the laser beam having a wavelength of 2.8 μm can be output from the distal end of the optical fiber cable 5, 9. Therefore, an effect equivalent to that for guiding a laser beam having a wavelength of 2.8 μm, which cannot be guided in the conventional device, along the optical fiber, can be expected. The present invention can greatly contribute to the advance of medical laser techniques since a laser beam having a wavelength of 2.8 μm at which water absorption characteristics are maximized can be obtained at the distal end of the optical fiber.

As described above, according to the arrangement of each of the above embodiments, in the solid-state laser device comprising the solid-state laser medium, even in a wavelength range which exceeds a wavelength of 2.5 μm and in which the generation wavelength of the solid-state laser medium cannot be easily guided along the optical fiber, a laser beam having the above-mentioned wavelength can be output at an arbitrary position using the optical fiber, and the practical effect of the laser device can be greatly improved, thus greatly contributing to widening of the application range of the solid-state laser device.

The present invention is not limited to the above embodiments and various changes and modifications can be made within the spirit and scope of the present invention. Therefore, to apprise the public of the scope of the present invention the following claims are made.

What is claimed is:

1. A solid-state laser device comprising:
   a solid-state laser device main body incorporating a semiconductor laser and a first optical system for shaping a first laser beam emitted from said semiconductor laser;
   an optical fiber cable connected to said solid-state laser device main body and accommodating an optical fiber for guiding the first laser beam shaped by said first optical system; and
   a solid-state laser medium which is incorporated in a distal end portion, at a light exit side, of said optical fiber cable, and generates a second laser beam by pumping the first laser beam, wherein said first laser beam has a wavelength which easily passes through said optical fiber, and said second laser beam has an infrared wavelength which can hardly pass through said optical fiber.

2. The device according to claim 1, wherein a wavelength of the first laser beam is different from a wavelength of the second laser beam.

3. The device according to claim 1, wherein the wavelength of the second laser beam is 2.8 μm.

4. The device according to claim 1, wherein said optical fiber cable is detachably connected to said solid-state laser device main body via a connector.

5. The device according to claim 1, further comprising a second optical system which is incorporated in the distal end portion, at the light exit side, of said optical fiber cable, shapes the first laser beam led to the distal end portion of said optical fiber, and guides the first laser beam to be incident on said solid-state laser medium.

6. The device according to claim 1, wherein a gap is formed between an outer circumferential surface of said optical fiber and an inner circumferential surface of said optical fiber cable, and a cooling medium for cooling said solid-state laser medium is circulated in said gap.

7. The device according to claim 6, wherein said cooling medium is an inert gas.

8. The device according to claim 6, wherein said cooling medium is air.

9. The device according to claim 6, wherein said optical fiber is fixed to the inner circumferential surface of said optical fiber cable via a holder.

10. The device according to claim 9, wherein said holder has a function of fixing said solid-state laser medium, said second optical system, and the distal end portion of said optical fiber on a single optical axis.

11. The device according to claim 9, wherein said holder comprises a fin for promoting cooling of said solid-state laser medium.

12. The device according to claim 1, wherein said solid-state laser device is used in a medical field.

13. The device according to claim 1, wherein said optical fiber cable has a substantially constant diameter throughout its whole length.

* * * * *

UNITED STATES PATENT AND TRADEMARK OFFICE
CERTIFICATE OF CORRECTION

PATENT NO. : 5,568,503

DATED : October 22, 1996

INVENTOR(S) : Shigeru OMORI

It is certified that error appears in the above-indentified patent and that said Letters Patent is hereby corrected as shown below:

On the title page, item [56], add the following:

|   |   |   |   |
|---|---|---|---|
| -- | 4,538,278 | 8/1985 | Gergely |
|  | 4,628,416 | 12/1986 | Dewey |
|  | 4,723,257 | 2/1988 | Baer et al |
|  | 4,819,630 | 4/1989 | DeHart |
|  | 5,311,528 | 5/1994 | Fujino |
|  | 5,318,562 | 6/1994 | Levy et al |
|  | 404369888 | 12/1992 | Japan    --. |

Signed and Sealed this

Thirtieth Day of September, 1997

Attest:

BRUCE LEHMAN

*Attesting Officer*    *Commissioner of Patents and Trademarks*